(12) United States Patent
Minato

(10) Patent No.: US 6,743,213 B1
(45) Date of Patent: Jun. 1, 2004

(54) DISPOSABLE DIAPER HAVING MECHANICAL FASTENING SYSTEM

(75) Inventor: Hironao Minato, Kanagawa-ken (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/259,687

(22) Filed: Mar. 1, 1999

(30) Foreign Application Priority Data

Mar. 9, 1998 (JP) .......................................... 10-056538

(51) Int. Cl.$^7$ .......................... A61F 13/15; A61F 13/20
(52) U.S. Cl. ...................................... 604/390; 604/391
(58) Field of Search ........................ 604/386, 389–391, 604/385.01; 24/306, 451; 428/100, 343

(56) References Cited

U.S. PATENT DOCUMENTS

| | | | | |
|---|---|---|---|---|
| RE26,151 E | * | 1/1967 | Duncan et al. | |
| 3,776,234 A | * | 12/1973 | Itoey | 604/390 |
| 3,885,566 A | * | 5/1975 | Jacob | 604/390 |
| 4,376,147 A | * | 3/1983 | Byrne et al. | 604/390 |
| 4,436,520 A | * | 3/1984 | Lipko et al. | 604/385.01 |
| 4,959,265 A | * | 9/1990 | Wood et al. | 604/389 |
| 4,985,025 A | * | 1/1991 | Lingertat et al. | 604/390 |
| 5,221,276 A | * | 6/1993 | Battrell | 604/391 |
| 5,288,546 A | * | 2/1994 | Roessler et al. | 604/391 |
| 5,383,872 A | * | 1/1995 | Roessler et al. | 604/391 |
| 5,399,177 A | * | 3/1995 | Blaney et al. | 604/389 |
| 5,476,702 A | * | 12/1995 | Datta et al. | 604/391 |
| 5,603,145 A | * | 2/1997 | Arakawa et al. | 24/442 |
| 5,611,789 A | * | 3/1997 | Seth | 604/391 |
| 5,636,414 A | * | 6/1997 | Litchholt | |
| 5,660,659 A | * | 8/1997 | Caldwell | 604/396 |
| 5,691,027 A | * | 11/1997 | Eckhardt et al. | 428/100 |
| 5,961,761 A | * | 10/1999 | Heindel et al. | 156/163 |
| 6,210,390 B1 | * | 4/2001 | Karlsson | 604/391 |
| 6,363,587 B1 | * | 4/2002 | Richter et al. | |
| 6,393,673 B1 | * | 5/2002 | Kourtidis et al. | |
| 6,419,667 B1 | * | 7/2002 | Avalon et al. | 604/391 |
| 6,428,525 B1 | * | 8/2002 | Malowaniec | 604/389 |
| 6,524,294 B1 | * | 2/2003 | Hilston et al. | 604/386 |

FOREIGN PATENT DOCUMENTS

| | | | | |
|---|---|---|---|---|
| DE | 296 22 981 | | 10/1997 | |
| EP | 0 418 954 | | 3/1991 | |
| EP | 0476992 | * | 3/1992 | .......... 604/389 |
| EP | 0 756 855 | | 2/1997 | |
| EP | 0 832 573 | | 4/1998 | |
| EP | 894 448 | | 2/1999 | |
| FR | 2624353 A1 | * | 6/1989 | .......... A41B/13/02 |
| WO | 98/29081 | * | 7/1998 | |

* cited by examiner

Primary Examiner—Karin Reichle
(74) Attorney, Agent, or Firm—Lowe Hauptman Gilman & Berner LLP

(57) ABSTRACT

A disposable diaper includes tape fasteners extending outward from transversely opposite side edges of the diaper and provided on their inner surfaces with hook members. The hook members have their inner surfaces partially coated with adhesive layers by which the hook members are peelably bonded to release zones defined in the proximity of the transversely opposite side edges of the diaper.

3 Claims, 4 Drawing Sheets

DISPOSABLE DIAPER HAVING MECHANICAL FASTENING SYSTEM

BACKGROUND OF THE INVENTION

The present invention relates to a disposable diaper having a mechanical fastening system.

Conventional disposable diapers are provided at transversely opposite side edges of a rear waist region of the diaper with a pair of tape fasteners for joining the side edges to transversely opposite side edges of a front waist region of the diaper. There are various types of tape fasteners used for the above purpose. For example, a tape fastener may comprise a base tape provided on its inner surface with an adhesive zone or a hook member adapted to be combined with a loop member to form a mechanical fastener. Disposable diapers are also known to have the side edges made of a plastic sheet, a nonwoven fabric or a laminate of a plastic sheet and a nonwoven fabric.

Disposable diapers provided with tape fasteners are usually supplied to consumers in the form of a package in which individual diapers are folded up with the tape fasteners folded back inwardly of the diapers and placed on the inner surfaces of the respective side edges of the diapers. In this manner, the adhesive zones and/or the hook elements of the fasteners can be protected from being contaminated by extraneous substances. Furthermore, the presence of the fasteners do not obstruct the diapers from being folded up. However, a serious problem should be encountered when the fasteners use hook members and the transversely opposite side edges of the diaper have their inner surfaces formed by plastic sheets. Specifically, it is impossible in such an arrangement to temporarily anchor the hook members to the foregoing inner surfaces and the fasteners may unintentionally shift to obstruct operation of folding up the diapers. Thus, extraneous substances may contaminate the inner surfaces of the fasteners.

SUMMARY OF THE INVENTION

In view of the problem as has been described above, it is an object of the present invention to provide a disposable diaper in which hook members employed in tape fasteners for the disposable diaper can be temporarily bonded to the inner surfaces of the diaper side edges.

According to the present invention, there is provided a disposable diaper comprising: a liquid-pervious topsheet, a liquid-impervious backsheet and a liquid-absorbent core disposed therebetween so as to form a first waist region, a second waist region and a crotch region extending therebetween; front surfaces in proximity of transversely opposite side edges of the first waist region including a release zone; the first waist region being provided on the transversely opposite side edges thereof with a pair of extensions; the extensions being provided on front surfaces thereof with hook members adapted to be engaged with loop members; the hook members having adhesive layers formed on front surfaces thereof; and the extensions being folded back inwardly of the diaper and peelably bonded to the release zones by the adhesive layers.

According to an embodiment of the present invention, the loop members are provided on a rear surface of the second waist region.

According to another embodiment of the present invention, the loop members are peelably engaged with the hook members on front surfaces of the loop members, the loop members being peelably bonded to the release layers by adhesive layers formed on rear surfaces of the loop members.

It should be noted here that the extensions, the hook members and the adhesive layers form tape fasteners.

In the disposable diaper according to the present invention, the presence of the tape fasteners does not obstruct the diaper from being rolled up for packaging or storage even when the tape fasteners use the hook members of a so-called mechanical fastener type. The reason for this is that each of the tape fasteners is provided on its inner surface with the adhesive layer by means of which the tape fastener can be temporarily bonded to the inner surface of the diaper.

In accordance with an aspect of the present invention, a disposable diaper is provided. The diaper has, in a longitudinal direction thereof, a front waist region, a rear second waist region and a crotch region extending therebetween. The diaper comprises a liquid-pervious topsheet; a liquid-impermeable backsheet extending transversely beyond a periphery of the top sheet in the rear waist region to form a pair of extended portions which define transversely opposite side edges of the rear waist region, respectively, wherein an outer surface of the backsheet defines an outer surface of the diaper, and an inner surface of the backsheet in the extended portions defines, together with an inner surface of the topsheet, an inner surface of the diaper; and a liquid-absorbent core disposed between the topsheet and backsheet. The diaper further comprises release zones defined solely by the inner surface of the backsheet in the extended portions, in proximity of the transversely opposite side edges of the rear waist region, respectively; and a pair of extensions provided on the transversely opposite side edges of the rear waist region, respectively. Hook members are provided on inner surfaces of the extensions, respectively. Adhesive layers are coated on inner surfaces of the hook members, respectively. The extensions, in a folded state, are folded back inwardly of the diaper and peelably bonded to the release zones by the adhesive layers, respectively. At least one loop member is provided on the outer surface of the diaper in the front waist region and adapted to be peelably engaged with the hook members. The backsheet is made of a plastic sheet.

Preferably, the hook members and the loop member constitute a mechanical fastener.

In accordance with another aspect of the present invention, a disposable diaper is provided. The disposable diaper has, in a longitudinal direction thereof, a front waist region, a rear second waist region and a crotch region extending therebetween. The diaper comprises a liquid-pervious topsheet; a liquid-impermeable backsheet extending transversely beyond a periphery of the top sheet in the rear waist region to form a pair of extended portions which define transversely opposite side edges of the rear waist region, respectively, wherein an outer surface of the backsheet defines an outer surface of the diaper, and an inner surface of the backsheet in the extended portions defines, together with an inner surface of the topsheet, an inner surface of the diaper; and a liquid-absorbent core disposed between the topsheet and backsheet. The diaper further comprises release zones defined by the inner surface of the backsheet in the extended portions, in proximity of the transversely opposite side edges of the rear waist region, respectively; and a pair of extensions provided on the transversely opposite side edges of the rear waist region, respectively. Hook members are provided on inner surfaces of the extensions, respectively. Adhesive layers are coated on inner surfaces of the hook members, respectively. The extensions, in a folded state, are folded back inwardly of the diaper and peelably bonded to the release zones by the adhesive layers, respectively. At least one loop member is provided on the outer surface of the diaper in the front waist region and adapted to be peelably engaged with the hook members. The backsheet includes a plastic sheet having an exposed surface defining the inner surface of the backsheet in the extended portions. The hook members have hooks mechanically engageable with loops of the loop member. The plastic sheet extends continuously uninterruptedly throughout the extended portions. The exposed surface of the plastic sheet defines the entire inner Surface of the backsheet in the extended portions, including the release zones.

DETAILED DESCRIPTION OF THE PREFERRED EMBODIMENTS

Details of a disposable diaper according to the present invention will be more fully understood from the description given hereunder with reference to the accompanying drawings.

Figure 1:
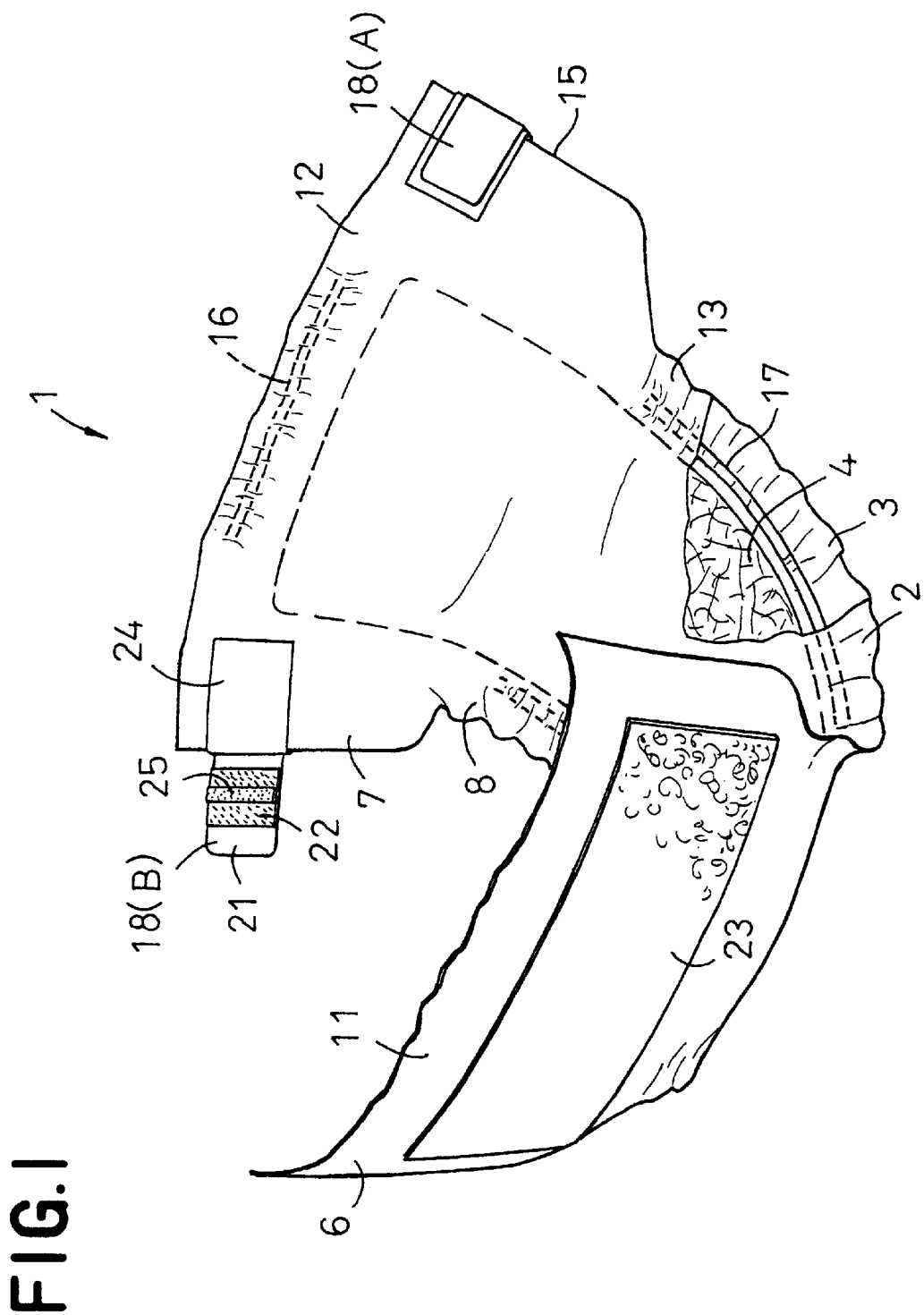
FIG. 1 is a perspective partially cut away view showing a disposable diaper according to the present invention.

Disposable diaper 1 shown by FIG. 1 in a perspective partially cut away view comprises a liquid-pervious topsheet 2, a liquid-impervious backsheet 3 and a liquid-absorbent core 4 disposed between these two sheets 2, 3. As viewed longitudinally, the diaper 1 is configured with a front waist region 6, a rear waist region 7 and a crotch region 8 extending between said two regions 6, 7. The topsheet 2 and the backsheet 3 extend outward beyond peripheral edges of the core 4 so as to be placed upon each other and bonded together along the respective extensions of two sheets 2, 3, forming respective end flaps 11, 12 of the front and rear waist regions 6, 7 and transversely opposite side edge flaps 13 extending between the front and rear waist region 6, 7. The end flap 12 and the side flaps 13 are provided with a transversely extending elastic member 16 and with longitudinally extending elastic members 17, respectively. These elastic members 16, 17 are laid between the topsheet 2 and the backsheet 3 and secured under appropriate tension to the inner surface of at least one of these two sheets 2, 3.

The rear waist region 7 of the diaper 1 is provided with a pair of tape fasteners 18 respectively extending outward from transversely opposite side edges 15 thereof and folded back onto the inner side of the diaper 1 before actual use of the diaper 1. It should be understood that these tape fasteners 18 are shown with the one 18(A) folded back inwardly of the diaper 1 and with the other 18(B) projecting outward.

Each of the tape fasteners 18 comprises a piece of base tape 21 having an inner end fixed to the rear waist region 7 in the proximity of the side edge 15 thereof, an outer free end projecting outward beyond the side edge 15, and a hook member 22 attached to the inner surface of the base tape 21. The hook member 22 is adapted to cooperate with a loop member 23 as will be described later in detail. These two members 22, 23 constitute together a so called mechanical fastener which is well known under various trade names such as VELCRO. The hook member 22 lies between the outer end of the base tape 21 and the side edge 15. A portion of the base tape 21 in the proximity of the outer end is used as a grip for the tape fastener 18.

The hook member 22 has its inner surface partially coated with pressure sensitive adhesive to define an adhesive zone 25. On the other hand, the rear waist region 7 is provided on its inner surface in the proximity of the side edge 15 with a release sheet 24 made of a plastic material allowing the adhesive zone 25 to be easily peeled off therefrom. In this manner, the tape fastener 18 may be folded back inwardly of the diaper 1 and then anchored to the release sheet 24 by means of the adhesive 25.

The front waist region 6 of the diaper 1 is provided with the loop member 23 made of a nonwoven fabric attached thereto. The diaper 1 is put on a wearer's body by peeling the tape fasteners 18 off the release sheets 24 and fastening the respective hook members 22 to the loop member 23. The loop member 23 is made of a nonwoven fabric having a relatively low fiber density so that areas over which the adhesive 25 of the respective hook members 22 acts on the loop member 23 can be adequately limited in order to ensure that the presence of the adhesive 25 should not obstruct desired smooth peeling of the hook members 22. The loop member 23 may be previously surface treated to facilitate peeling of adhesive 25 off the surface of the loop member 23.

With the diaper 1 constructed as has been described above, the tape fasteners 18 extending outward from the transversely opposite side edges of the diaper 1 are folded back and temporarily bonded to the inner side of the diaper 1 before actual use thereof. Accordingly, the presence of these tape fasteners 18 does not obstruct the diaper 1 from being folded up. When the used diaper 1 is disposed, the used diaper 1 may be rolled up and then an adhesive force of the tape fasteners 18 may be utilized to hold the diaper in a rolled up state.

Figure 2:
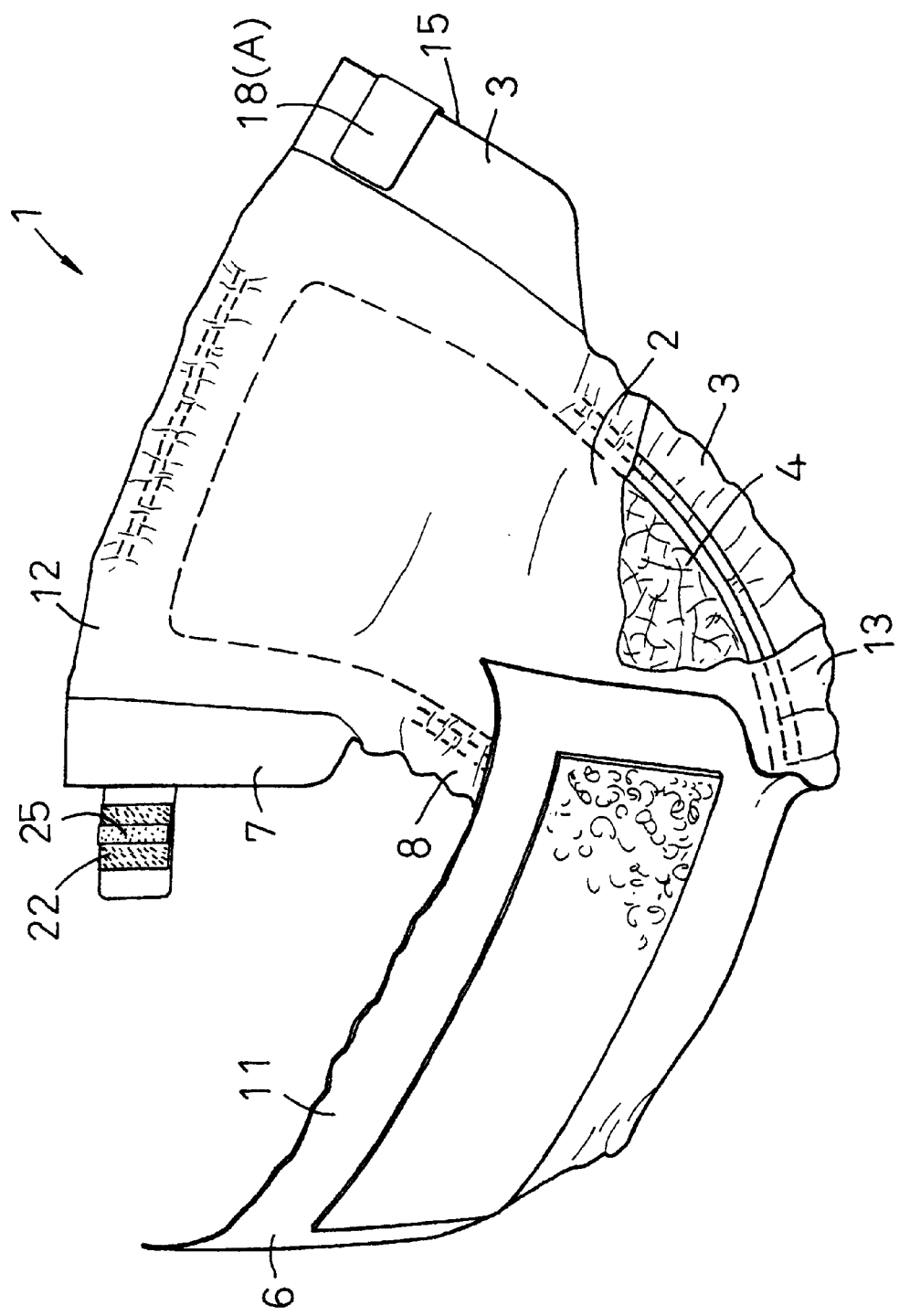
FIG. 2 is a view similar to FIG. 1 showing an embodiment of the invention.

FIG. 2 is a view similar to FIG. 1 showing an embodiment according to the present invention. With the diaper 1 according to this embodiment, the backsheet 3 made of a plastic sheet extends outward further than the topsheet 2 along the side flaps 13 of the rear waist region 7. The tape fasteners 18 folded back inwardly of the diaper 1 are placed upon the inner surface of the backsheet 3 and temporarily bonded to the inner surface by means of the adhesive 25 in the proximity of the side edges of the rear waist region 7. The inner surface of the backsheet 3 may be previously surface treated to facilitate peeling of the adhesive 25 therefrom.

Figure 3:
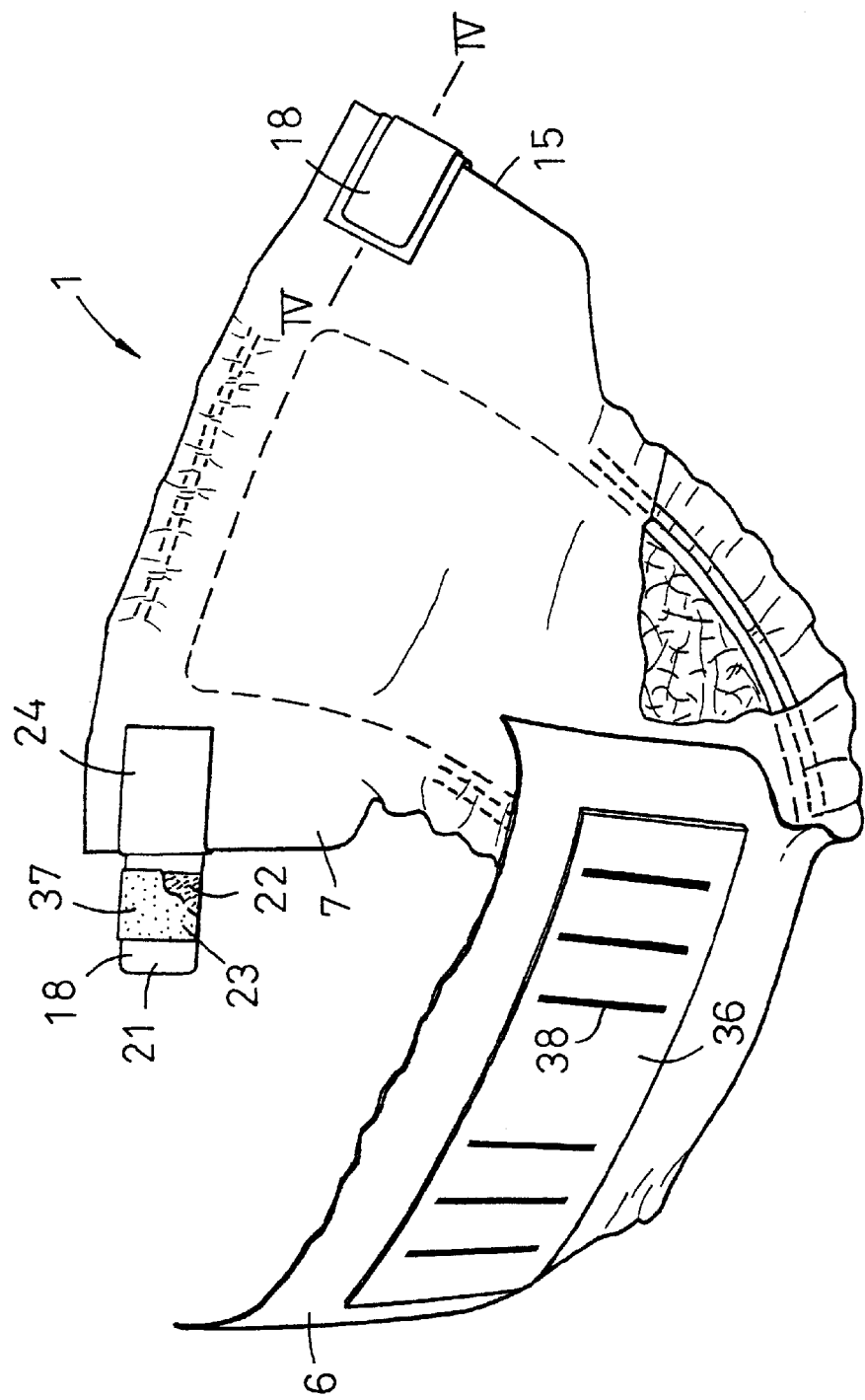
FIG. 3 is a view similar to FIG. 2 showing another embodiment of the present invention.
Figure 4:
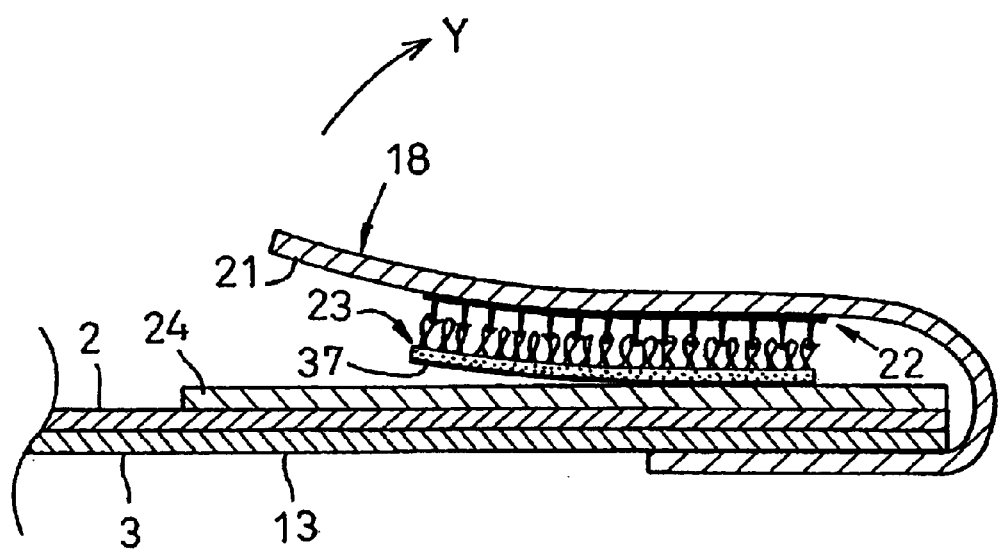
FIG. 4 is a sectional view taken along line IV—IV in FIG. 3.

FIG. 3 is a view similar to FIG. 1 showing still another embodiment of the present invention and FIG. 4 is a sectional view taken along line IV—IV in FIG. 3. FIG. 4 shows the tape fastener 18 being folded back in the direction as indicated by an arrow Y. With the diaper 1 according to this embodiment, the tape fastener 18 is provided on the inner surface of the base tape 21 with the hook member 22 and relatively small individual loops of the loop member 23 are peelably bonded on the surface of the hook member 22. The surface of the loop member 23 opposed to the loops is coated with adhesive 37 to define an adhesive zone. The tape fastener 18 is folded back inwardly of the diaper 1 and bonded to the release sheet 24 provided on the rear waist region 7 in the proximity of the side edge 15 by means of the adhesive 37. In the front waist region 6 of the diaper 1, the backsheet 3 made of a plastic sheet is provided on its outer surface with a plastic sheet 36 to which the loop member 23 is fixed. The tape fastener 18 peeled off from the release sheet 24 may be moved together with the loop member 23 bonded thereto to the outer surface of the front waist region 6. Then, an appropriate index 38 may be selected from a plurality of position-indices 38 printed on the plastic sheet 36 serving to fix the loop member 23 and this loop member 23 may be fixed to the position corresponding to the selected index 38 by means of the adhesive 37. In this way, the tape fastener 18 may be separably fixed to the plastic sheet 36 fixed to the front waist region 6. The plastic sheet 36 serves also as a reinforcing member adapted to prevent the backsheet 3 from being broken or torn even if fixation and peeling off are repeated.

The diaper 1 according to the present invention may also employ a nonwoven fabric or an apertured plastic sheet as the topsheet 2, and a plastic sheet or paper as the base tape 21.

What is claimed is:

1. A disposable diaper having, in a longitudinal direction thereof, a front waist region, a rear second waist region and a crotch region extending therebetween, said diaper comprising:

a liquid-pervious topsheet;

a liquid-impermeable backsheet extending transversely beyond a periphery of said top sheet in said rear waist region to form a pair of extended portions which define transversely opposite side edges of said rear waist region, respectively, wherein an outer surface of said backsheet defines an outer surface of said diaper, and an inner surface of said backsheet in the extended portions defines, together with an inner surface of said topsheet, an inner surface of said diaper;

a liquid-absorbent core disposed between said topsheet and backsheet;

release zones defined solely by the inner surface of said backsheet in the extended portions, in proximity of the transversely opposite side edges of said rear waist region, respectively;

a pair of extensions provided on the transversely opposite side edges of said rear waist region, respectively;

hook members provided on inner surfaces of said extensions, respectively;

adhesive layers coated on inner surfaces of said hook members, respectively;

said extensions, in a folded state, being folded back inwardly of said diaper and peelably bonded to said release zones by said adhesive layers, respectively; and at least one loop member provided on the outer surface of said diaper in said front waist region and adapted to be peelably engaged with said hook members;

wherein said backsheet is made of a plastic sheet.

2. The disposable diaper according to claim 1, wherein the hook members and the loop member constitute a mechanical fastener.

3. A disposable diaper having, in a longitudinal direction thereof, a front waist region, a rear second waist region and a crotch region extending therebetween, said diaper comprising:

a liquid-pervious topsheet;

a liquid-impermeable backsheet extending transversely beyond a periphery of said top sheet in said rear waist region to form a pair of extended portions which define transversely opposite side edges of said rear waist region, respectively, wherein an outer surface of said backsheet defines an outer surface of said diaper, and an inner surface of said backsheet in the extended portions defines, together with an inner surface of said topsheet, an inner surface of said diaper;

a liquid-absorbent core disposed between said topsheet and backsheet;

release zones defined by the inner surface of said backsheet in the extended portions, in proximity of the transversely opposite side edges of said rear waist region, respectively;

a pair of extensions provided on the transversely opposite side edges of said rear waist region, respectively;

hook members provided on inner surfaces of said extensions, respectively;

adhesive layers coated on inner surfaces of said hook members, respectively;

said extensions, in a folded state, being folded back inwardly of said diaper and peelably bonded to said release zones by said adhesive layers, respectively; and at least one loop member provided on the outer surface of said diaper in said front waist region and adapted to be peelably engaged with said hook members;

wherein said backsheet includes a plastic sheet having an exposed surface defining the inner surface of said backsheet in the extended portions;

said hook members have hooks mechanically engageable with loops of said loop member;

said plastic sheet extends continuously uninterruptedly throughout the extended portions; and the exposed surface of said plastic sheet defines the entire inner surface of said backsheet in the extended portions, including said release zones.

* * * * *